United States Patent
Bonrath et al.

(10) Patent No.: US 7,842,841 B2
(45) Date of Patent: Nov. 30, 2010

(54) PROCESS FOR THE PREPARATION OF TIMBERONE

(75) Inventors: Werner Bonrath, Freiburg (DE); Jan Schuetz, Loerrach (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/532,419

(22) PCT Filed: Mar. 17, 2008

(86) PCT No.: PCT/EP2008/002120

§ 371 (c)(1),
(2), (4) Date: Nov. 11, 2009

(87) PCT Pub. No.: WO2008/113545

PCT Pub. Date: Sep. 25, 2008

(65) Prior Publication Data

US 2010/0063325 A1    Mar. 11, 2010

(30) Foreign Application Priority Data

Mar. 22, 2007    (EP) ................................. 07005910

(51) Int. Cl.
*C07C 45/00* (2006.01)
(52) U.S. Cl. ..................................................... 568/345
(58) Field of Classification Search ................... 568/345
See application file for complete search history.

(56) References Cited

U.S. PATENT DOCUMENTS 4,252,986 A        2/1981   Klein et al.
2007/0032685 A1*   2/2007   Schatkowski ............... 568/822

FOREIGN PATENT DOCUMENTS

EP          0 118 809           9/1984

OTHER PUBLICATIONS

International Search Report for PCT/EP2008/002120, mailed Jun. 9, 2008.
Written Opinion of the International Searching Authority for PCT/EP2008/002120, mailed Jun. 9, 2008.

* cited by examiner

*Primary Examiner*—Sikarl A Witherspoon
(74) *Attorney, Agent, or Firm*—Nixon & Vanderhye P.C.

(57) ABSTRACT

This invention relates to a novel process for the preparation of timberone useful for perfume or cosmetics.

8 Claims, No Drawings

PROCESS FOR THE PREPARATION OF TIMBERONE

This application is the U.S. national phase of International Application No. PCT/EP2008/002120, filed 17 Mar. 2008, which designated the U.S., and claims priority to EP 07005910.0, filed 22 Mar. 2007, the entire contents of each of which are hereby incorporated by reference.

This invention relates to a novel process for the preparation of timberone useful for perfume or cosmetics.

Timberone is known to have a woody/amber-like odour which is highly appreciated by the fragrance industry.

EP 0118809 discloses a three step process for the preparation of timberone starting with β-cyclocitral: β-cyclocitral is catalytically hydrogenated to give a cis/trans mixture of 1-formyl-2,6,6,-trimethyl-cyclohexane. The addition of 2-pentanone to dihydro-cyclocitral in the presence of a strong base results in 1-(2,6,6,-trimethylcyclohexyl)-1-hexen-3-one which is afterwards hydrogenated to give timberone. However, β-Cyclocitral is not readily available and rather expensive and thus an alternative route using readily available and cheap raw materials would be highly desirable.

Thus, there is an ongoing need for an efficient and economical attractive process for the preparation of timberone (1) [chemical name: 1-(2,2,6-trimethylcyclohexyl)-hexan-3-one].

Surprisingly it has been found that timberone can be prepared starting with cheap and readily available citral in a three step process with a high overall yield as depicted below:

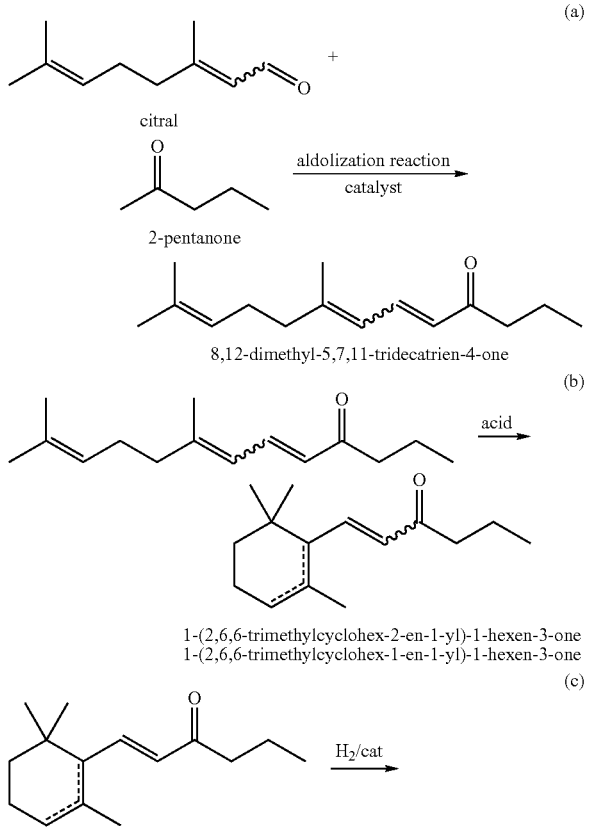

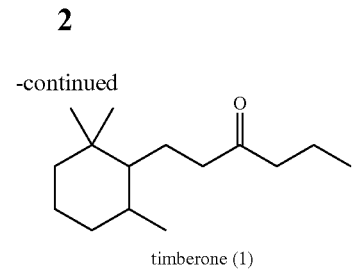

timberone (1)

Thus, the invention relates to a process for the preparation of timberone (1), the process comprising the step of
  (a) reacting citral with a 2-pentanone in the presence of an aldolization catalyst to produce 8,12-dimethyl-5,7,11-tridecatrien-4-one and
  (b) cyclization of 8,12-dimethyl-5,7,11-tridecatrien-4-one in the presence of an acid to 1-(2,6,6-trimethylcyclohex-2-en-1-yl)-1-hexen-3-one and/or 1-(2,6,6-trimethylcyclo-hex-1-en-1-yl)-1-hexen-3-one and
  (c) hydrogenation of 1-(2,6,6-trimethylcyclohex-2-en-1-yl)-1-hexen-3-one and/or 1-(2,6,6-trimethylcyclohex-1-en-1-yl)-1-hexen-3-one in the presence of Pt and for Pd catalyst to timberone.

Wherein the dotted line indicates a double bond which can be arranged in one of the two indicated positions. According to the nomenclature used for ionones they can also be referred to as α or β double bond (see Römpp-Lexikon Naturstoffe, Thieme, 1997, page 334-335)

The timberone of formula (1) (i.e. the 1-(2,2,6-trimethyl-cyclohexan-1-yl)-1-hexan-3-one) obtainable via the process according to the invention may encompasses 4 different stereoisomers. Dependent on the reaction conditions, the timberone can be present in a stereochemically pure form or as a mixture of two or several stereoisomers in variable ratios.

The term 'aldolization catalyst' as used in the present invention refers to catalysts being capable to catalyse aldol condensation reactions i.e. the addition of ketones and/or aldehydes to obtain aldols (β-hydroxy ketones) followed by dehydration of the resulting aldol to obtain a α,β-unsaturated ketones.

Suitable aldolization catalyst to be employed in step (a) of the process according to the invention are any heterogeneous or homogeneous aldolization catalyst known to a skilled person in the art. Exemplary aldolization catalysts encompass bases such as sodium hydroxide or potassium hydroxide, ion exchangers or supported catalysts. In all embodiments of the invention, preferred aldolization catalyst are heterogeneous aldolization catalysts i.e. supported catalyst which can be filtered off after the reaction is completed. In particular preferred are basic silica supported aldolization catalyst.

In all embodiments according to the invention the use of Ca/Na on silica ($SiO_2$) as aldolization catalyst is preferred, especially a catalyst with a surface area<500 $m^2/g$, in particular with a surface area<200 $m^2/g$, and a metal loading of about 15 to 35 wt.-% Ca and about 20 to 35 wt.-% Na based on the total weight of the catalyst, preferably with a metal loading of about 20 to 30 wt.-% Ca and about 24 to 32 wt.-% Na.

In another preferred embodiment, the aldolization catalyst is selected from alkali hydroxides in an aqueous-organic phase or sodium ethoxide in an organic phase such as e.g. ethanol.

The preparation of supported aldolization catalysts is well known to a person skilled in the art. For example, the basic silica supported catalyst which may be used in the process according to the invention is obtainable as e.g. disclosed in WO01/87812.

Ca/Na on silica is e.g. obtainable by impregnating a silica support with an aqueous solution of a calcium compound, optionally and preferably in the presence of a sodium compound followed by drying and calcinations if necessary to effect decomposition to the respective basic compounds. As calcium and sodium compound any compounds which are basic or decompose to a basic compound upon heating such as for example calcium/sodium hydroxide, acetate, oxalate, nitrate or carbonate may be used. As silica support any silica may be used such as e.g. silica support based on natural raw material or fumed pyrogenic silica which is e.g. available as Aerosil®/Aerolyst® from Degussa AG, Hanau, Germany. In all embodiments of the invention, the Ca/Na on silica catalyst preferably has a metal loading of about 15 to 35 wt.-% Ca and about 20 to 35 wt.-% Na based on the total weight of the catalyst, more preferably a metal loading of about 20 to 30 wt.-% Ca and about 24 to 32 wt.-% Na.

The supported aldolization catalyst may be used as such or it may be suspended prior to its use. In a preferred embodiment of the invention the supported aldolization catalyst is added to the reaction mixture in pure solid form without further activation or modification. After termination of the reaction the catalyst can be recycled by simple technical measures such as filtration or decantation. The amount of the supported catalyst used in the process according to the invention is based on the amount of citral. In all embodiments of the invention, the amount of the supported aldolization catalyst is in the range of 5 to 30 wt %, preferably from 10 to 20 wt.-%, in particular in the range of 18 wt.-% based on citral. Such amounts of the supported aldolization catalyst are sufficient to obtain high yields of desired product.

The aldolization reaction according to the invention can be carried out without an additional solvent or in the presence of an additional solvent. Suitable solvents for the aldol condensation reaction are non-polar aprotic solvents, e.g. toluene, xylene, or ethers, e.g. diethyl ether methyl t-butyl ether. Preferably, in all embodiments of the invention, the reaction is carried out without the addition of an additional solvent. The ratio of 2-pentanone to citral is not critical for the reaction and can vary over a wide range, although 2-pentanone is normally used as excess component in order to achieve high product selectivity in relation to citral. Good results are obtained if a molar ratio of the citral to the 2-pentanone of 1:0.5 to 1:50, preferably 1:1 to 1:30, most preferably in the range of 1:10 to 1:3, in particular in the range of 1:4.4 is used.

Thus, in a preferred embodiment, the invention relates to a process according to the invention wherein the molar ratio of the citral to the 2-pentanone is selected in the range of 1:0.5 to 1:50, preferably 1:1 to 1:30, most preferably in the range of 1:10 to 1:3, in particular in the range of 1:4.4

The cyclization of 8,12-dimethyl-5,7,11-tridecatrien-4-one can be performed in the presence of an acid such as e.g. a liquid acid (e.g. $H_3PO_4$ or $MeSO_3H$) or a solid acid (acidic ion exchange). Preferably, the acid is selected from $H_3PO_4$ or a sulphur containing acid such as $H_2SO_4$, $MeSO_3H$ or $F_3CSO_3H$. Preferably, the cyclization is performed in the presence of a sulfur containing acid, in particular in the presence of $MeSO_3H$. The use of a sulfur containing acid leads to the preferred formation of the β-isomer 1-(2,6,6-trimethylcyclohex-1-en-1-yl)-1-hexen-3-one. The ratio of α to β isomers is in the range of 30:60 to 1:99 wt.-%. The cyclization according to the invention can be carried out without an additional solvent or in the presence of an additional solvent. Suitable solvents for the cyclization reaction are non-polar aprotic solvents, e.g. pentane, hexane, heptane, octane, cyclohexane without being limited thereto. Preferably, the reaction is carried out in the presence of heptane. The temperature range for the cyclization reaction can be easily determined by a person skilled in the art and depends on the catalyst used. Preferably, the cyclization reaction is carried out at low temperature in particular at a temperature selected in the range of −10 to 20° C., in particular in the range of −5 to 10° C.

Surprisingly it has been found, that the carbon carbon double bonds of 1-(2,6,6-trimethylcyclohex-2-en-1-yl)-1-hexen-3-one and/or 1-(2,6,6-trimethylcyclohex-1-en-1-yl)-1-hexen-3-one can be selectively hydrogenated to timberone in the presence of a Pd or Pt catalyst in high yields without reducing the carbonyl group. Further unexpected, it has been found that both forms (α and/or β isomers) could be hydrogenated likewise to (all-rac)-timberone in quantitative yield at room temperature and low hydrogen pressure. Thus, the formation of the α- and/or β-form in the cyclization step does not necessarily have to be selective. Thus, in all embodiments of the invention suitable hydrogenation catalysts are Pt and/or Pd catalyst, in particular Pd catalyst on a solid support such as on carbon, alumina or silica, in particular Pd on carbon or Pd on alumina, more in particular Pd on carbon. The amount of the metal Pd or Pt on the solid support may vary in the range of 0.1 to 20 wt.-%, preferably in the range of 1 to 10 wt.-% such as 1, 5 or 10 wt.-%.

The amount of the hydrogenation catalyst used in the reaction is not critical and can be easily established by a person skilled in the art. Preferably, an amount of 2 to 10 wt.-%, more preferably an amount of 6 to 9 wt.-% based on the 1-(2,6,6-trimethylcyclohex-2-en-1-yl)-1-hexen-3-one and/or 1-(2,6,6-trimethylcyclohex-1-en-1-yl)-1-hexen-3-one is used. The hydrogenation reaction can be carried out without an additional solvent or in the presence of an additional solvent. Suitable solvents for the hydrogenation reaction are linear or cyclic hydrocarbon solvents, e.g. pentane, hexane, heptane or cyclohexane, aromatic hydrocarbons, e.g. toluene, xylene without being limited thereto. The temperature range for the hydrogenation can be easily determined by a person skilled in the art and depends on the catalyst and/or solvent used. Normally, the reaction is carried out at room temperature (i.e. 20-25° C.) or at elevated temperatures such as e.g. 50-100° C. The hydrogenation can either be performed at normal pressure or at elevated pressure such as e.g. at 1 to 10 bar.

The α0 and β isomer can be equally hydrogenated by the hydrogenation catalyst according to the invention in high yields.

Each reaction of the process according to the invention can in principle be carried out in any reactor suitable for the respective reaction type. Without restricting generality, the following are mentioned by way of example: suspension reactor, stirred tank, stirred tank cascade, tubular reactor, shell-type reactor, shell and tube reactor, fixed-bed reactor, fluidized-bed reactor, reactive distillation column.

The invention is illustrated further by the examples without being limited thereto

EXAMPLE 1

Step (a), Aldol Condensation

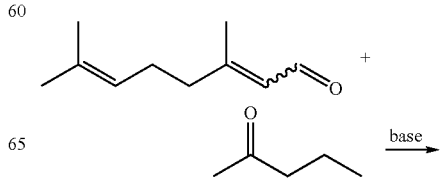

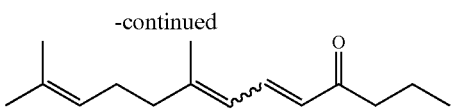

In a typical procedure for the aldol condensation citral (50 g, 91.4%, 300 mmol) and 2-pentanone (180 g, 90.0%, 1881 mmol) were stirred under argon in a 2-neck-flask at −10° C. Over 30 min a mixture of sodium (3.7 g, 161 mmol) in 68 ml ethanol was added. After the addition the mixture was stirred for 30 min at −10 to −5° C. A solution of tartaric acid (12.0 g, 99.5%, 80 mmol) in 60 ml of water was added. The aqueous phase was separated and the organic phase three times washed with a saturated aqueous NaCl solution (3×70 ml), dried with $Na_2SO_4$ and the solvent evaporated in vacuum. The raw product (81.2 g) was vacuum distilled. 8,12-Dimethyl-5,7,11-tridecatrien-4-one boils at 120-122° C. ($3.1×10^{-1}$ mbar). Yield: 65.7% (50.3 g, 86.7%, determined by GC, E/Z-mixture).

Alternative Procedure

Citral (2.0 g, 95.0%, 12.5 mmol) and 2-pentanone (20 g, 99.0%, 229.9 mmol) were stirred under argon in a 2-neck-flask at 80° C. Afterwards, Ca/Na on silica (360 mg, 18 wt % on citral) was added. The mixture was stirred for 4 h at 80° C. After cooling to room temperature the mixture was filtered, the heterogeneous catalyst washed with 2-pentanone and all volatiles of the liquid phase were removed in vacuum (20 mbar, 40° C.). Yield: 87.5% (3.81 g, 63.3%, determined by GC, E/Z-mixture).

$^1$H-NMR (300 MHz, $CDCl_3$): δ=7.47 (dd, J=11.5 Hz, 14.2 Hz, HC (6)); 7.44 (dd, J=11.5 Hz, 15.2 Hz, HC (6)); 6.11 (d, J=15.3 Hz, HC (5) or HC (7)); 6.07 (d, J=15.2 Hz, HC (5) or HC (7)); 5.99 (d, J=11.4 Hz, HC (5) or HC (7)); 5.12 (m, HC (11)); 2.53 (t, J=7.3 Hz, $H_2C$ (3) or $H_2C$ (9)); 2.52 (t, J=7.2 Hz, $H_2C$ (3) or $H_2C$ (9)); 2.32 (t, J=7.9 Hz, $H_2C$ (3) or $H_2C$ (9)); 2.16 (s, $CH_3$), 1.90 (s, $CH_3$), 1.68 (m, $CH_2$, $H_2C$ (2) and $H_2C$ (10)); 1.61 (s, $CH_3$), 0.95 (t, J=7.4 Hz, $H_3C$ (1));

$^{13}$C-NMR (75 MHz, $CDCl_3$): δ=201.0 (CO), 150.9 (C=C), 150.9 (C=C), 138.6 (C=C), 138.4 (C=C), 132.6 (C=C), 132.2 (C=C), 127.6 (C=C), 127.4 (C=C), 124.7 (C=C), 123.8 (C=C), 123.3 (C=C), 123.2 (C=C), 42.8, 42.7, 40.4, 33.0, 26.9, 26.3, 25.7, 24.6, 18.0, 17.9, 17.7, 17.5, 13.9.

EXAMPLE 2

Step (b), Cyclization

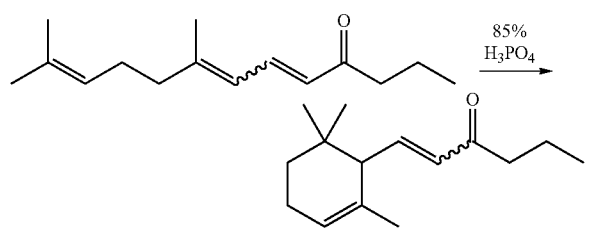

In a typical procedure with phosphoric acid, 8,12-dimethyl-5,7,11-tridecatrien-4-one (10.0 g, 86.7%, 39 mmol) was added drop wise to 50 ml $H_3PO_4$ (aq., 85%) at room temperature. The temperature rose during the addition from 23-24° C. to 32-33° C. After completion the mixture was stirred for additional 40 min at room temperature. The mixture was poured on 50 g ice and the organic phase extracted with ethyl acetate (3×50 ml). The combined organic phases were washed with 70 ml water and 70 ml saturated aqueous $NaHCO_3$ solution, dried over $Na_2SO_4$ and the solvent was evaporated in vacuum. The raw product (9.9 g) was vacuum distilled. 1-(2,6,6-Trimethylcyclohex-2-en-1-yl)-1-hexen-3-one boils at 96-97° C. ($3.1×10^{-1}$ mbar). Yield: 56.4% (6.9 g, 70.4% α-product and 13.8% β-product, determined by GC, E/Z-mixture)

$^1$H-NMR (300 MHz, $CDCl_3$): δ=6.63 (dd, J=9.7 Hz, 15.8 Hz, HC (1)); 6.09 (d, J=15.1 Hz, HC (2)); 5.49 (br, HC (3')); 2.53 (t, J=7.5 Hz, $H_2C$ (4)); 2.27 (d, J=9.7 Hz, HC (1')); 2.04 (m, $CH_2$), 1.3-1.1 (m, 7 H); 0.95 (t, J=7.2 Hz, $H_3C$ (6)); 0.93 (s, $H_3C$ (6)); 0.87 (s, $H_3C$—C (6'));

$^{13}$C-NMR (75 MHz, $CDCl_3$): δ=200.6 (CO), 147.8 (C=C), 132.0 (C=C), 131.6 (C=C), 122.5 (C=C), 54.3, 41.9, 32.5, 31.2, 27.8, 26.8, 23.0, 22.8, 17.8, 13.8.

Alternative Procedure:

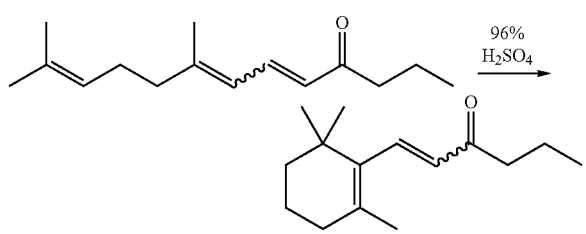

In a typical procedure with sulfuric acid, a solution of 8,12-dimethyl-5,7,11-tridecatrien-4-one (15.0 g, 86.7%, 59 mmol) in 15 ml heptane was cooled to −6° C. and added drop wise to a mixture of 47 g $H_2SO_4$ (96%) and 45 ml heptane at −10-20° C. The reaction mixture was stirred mechanically with 600 r/min. After 20 min the addition was completed and the mixture stirred for additional 60 min. During this time the mixture was slowly warmed to 0° C. The reaction mixture was poured on 80 g ice and the aqueous phase was separated and extracted with heptane (2×35 ml). The combined organic phases were washed with 40 ml saturated aqueous NaCl solution, 40 ml saturated aqueous $NaHCO_3$ solution, saturated aqueous NaCl solution (3×35 ml, until the aqueous phase became neutral), dried over $Na_2SO_4$ and the solvent evaporated in vacuum. The raw product (14.6 g) was vacuum distilled. 1-(2,6,6-Trimethylcyclohex-1-en-1-yl)-1-hexen-3-one boils at 98-102° C. ($2.0×10^{-1}$ mbar). Yield: 51.9% (8.1 g, 1.0% α-product and 99.0% β-product, determined by GC, E/Z-mixture).

$^1$H-NMR (300 MHz, $CDCl_3$): δ=7.29 (dd, J=16.4 Hz, HC (1)); 6.13 (d, J=16.3 Hz, HC (2)); 2.55 (t, J=7.3 Hz, $H_2C$ (4)); 2.17 (dd, J=6.2 Hz, $H_2C$ (3')); 1.76 (s, $H_3C$—C (2')), 1.69 (m, $H_2C$ (5)), 1.65 (m $H_2C$ (4') or $H_2C$ (5')); 1.18 (s, 6H, $H_3C$—C (6')); 0.96 (t, J=7.4 Hz, $H_3C$ (6));

$^{13}$C-NMR (75 MHz, $CDCl_3$): δ=200.9 (CO), 142.0 (C=C), 136.1 (C=C), 135.7 (C=C), 130.7 (C=C), 42.5, 39.7, 34.1, 33.5, 28.8, 22.7, 21.7, 18.9, 18.0, 13.9.

The same experiment as described above was repeated with further sulfur containing acids. The results are summarized in Table 1 below:

TABLE 1

| catalyst | solvent | reaction time | T [° C.] | yield (GC) | ratio α-isomer | β-isomer |
|---|---|---|---|---|---|---|
| $H_2SO_4$ | heptane | 80 min | −5 to −10 | 52% | 1.0% | 99.0% |
| $H_3PO_4$ | — | 50 min | r.t. | 56% | 85.4% | 14.6% |
| $MeSO_3H$ | heptane | 50 min | 10 | 87% | 32.5% | 67.5% |
| $F_3CSO_3H$ | heptane | 60 min | −15 | 65% | 8.2% | 91.8% |

As can be seen from the results, sulfur containing acid lead in a pre-dominant formation of the β-isomer. Furthermore, the use of methylsulfonic acid gave the highest yields.

EXAMPLE 3

Step (c), Hydrogenation

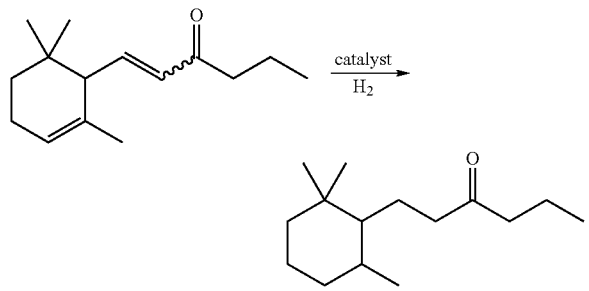

In a typical procedure for the hydrogenation, a solution of 1-(2,6,6-trimethylcyclohex-2-en-1-yl)-1-hexen-3-one (3 g, 87.5%, 12 mmol) and 35 ml cyclohexane was purged with hydrogen in a two-neck flask with 250 mg palladium on carbon (e.g. 10% Pd on C). The mixture was stirred at room temperature under a hydrogen atmosphere (1 bar) for 16 h. Initially the temperature rose from 25° C. to 29° C. After 60 min reaction time the temperature decreased to 25 C. The mixture was filtered and the solvent removed in vacuo. Yield: 91.2%, 3.1 g (78.6% determined by GC, the product is a mixture of diastereomers)

$^1$H-NMR (300 MHz, $CDCl_3$): δ=2.37 (t, J=7.7 Hz, $H_2C$ (4)); 2.0-0.8 (m, 26 H);

$^{13}$C-NMR (75 MHz, $CDCl_3$): δ=211.6 (CO), 49.2, 44.7, 34.3, 30.3, 19.4, 17.3, 13.8.

The invention claimed is:

1. A process for the preparation of timberone, the process comprising the step of
    reacting citral with a 2-pentanone in the presence of an aldolization catalyst to produce 8,12-dimethyl-5,7,11-tridecatrien-4-one and
    cyclization of 8,12-dimethyl-5,7,11-tridecatrien-4-one in the presence of an acid to 1-(2,6,6-trimethylcyclohex-2-en-1-yl)-1-hexen-3-one and/or 1-(2,6,6-trimethylcyclohex-1-en-1-yl)-1-hexen-3-one and
    hydrogenation of 1-(2,6,6-trimethylcyclohex-2-en-1-yl)-1-hexen-3-one and/or 1-(2,6,6-trimethylcyclohex-1-en-1-yl)-1-hexen-3-one in the presence of a Pt and for Pd catalyst.

2. The process according to claim 1, wherein the aldolization catalyst is a base supported on silica catalyst.

3. The process according to claim 1, wherein the aldolization catalyst is Ca/Na on silica.

4. The process according to claim 1, wherein the molar ratio of citral to
    2-pentanone is in the range of 1:0.5 to 1:50, preferably 1:1 to 1:30, most preferably in the range of 1:10 to 1:3.

5. The process according to claim 1, wherein the acid is a sulphur containing acid.

6. The process according to claim 5, wherein the sulphur containing acid is methylsulfonic acid.

7. The process according to claim 1, wherein the hydrogenation catalyst is Pd.

8. The process according to claim 7, wherein the hydrogenation catalyst is Pd on carbon or Pd on alumina.

* * * * *